US009974861B2

(12) United States Patent
Johnsson et al.

(10) Patent No.: US 9,974,861 B2
(45) Date of Patent: May 22, 2018

(54) PEPTIDE SLOW-RELEASE FORMULATIONS (75) Inventors: Markus Johnsson, Lund (SE); Fredrik Joabsson, Lund (SE); Catalin Nistor, Lund (SE); Krister Thuresson, Lund (SE); Fredrik Tiberg, Lund (SE)

(73) Assignee: CAMURUS AB (SE)

( * ) Notice: Subject to any disclaimer, the term of this patent is extended or adjusted under 35 U.S.C. 154(b) by 438 days.

(21) Appl. No.: 12/664,835

(22) PCT Filed: Jun. 13, 2008

(86) PCT No.: PCT/GB2008/002035
§ 371 (c)(1),
(2), (4) Date: Apr. 6, 2010

(87) PCT Pub. No.: WO2008/152401
PCT Pub. Date: Dec. 18, 2008

(65) Prior Publication Data
US 2010/0210519 A1    Aug. 19, 2010

(30) Foreign Application Priority Data
Jun. 15, 2007    (GB) .................................. 0711656.9

(51) Int. Cl.
*A61K 38/31* (2006.01)
*A61K 47/34* (2017.01)
*A61K 9/00* (2006.01)
*A61K 9/08* (2006.01)
*A61K 47/10* (2017.01)
*A61K 47/14* (2017.01)
*A61K 47/24* (2006.01)
*A61K 47/08* (2006.01)

(52) U.S. Cl.
CPC ............ *A61K 47/34* (2013.01); *A61K 9/0019* (2013.01); *A61K 9/08* (2013.01); *A61K 38/31* (2013.01); *A61K 47/08* (2013.01); *A61K 47/10* (2013.01); *A61K 47/14* (2013.01); *A61K 47/24* (2013.01)

(58) Field of Classification Search
CPC ....... A61K 51/083; A61K 38/16; A61K 38/31
See application file for complete search history.

(56) References Cited

U.S. PATENT DOCUMENTS

| | | | |
|---|---|---|---|
| 4,938,763 A | | 7/1990 | Dunn et al. |
| 5,340,802 A | * | 8/1994 | Shiosaki et al. ............. 514/12.6 |
| 5,480,656 A | | 1/1996 | Okada et al. |
| 5,531,925 A | | 7/1996 | Landh et al. |
| 5,639,480 A | | 6/1997 | Bodmer et al. |
| 5,776,885 A | | 7/1998 | Orsolini et al. |
| 5,807,573 A | | 9/1998 | Ljusberg-Wahren et al. |
| 5,955,502 A | | 9/1999 | Hansen et al. |
| 6,066,328 A | | 5/2000 | Ribier et al. |
| 6,113,943 A | | 9/2000 | Okada et al. |
| 6,228,383 B1 | | 5/2001 | Hansen et al. |
| 6,458,924 B2 | | 10/2002 | Knudsen et al. |
| 6,464,987 B1 | | 10/2002 | Fanara et al. |
| 8,097,239 B2 | | 1/2012 | Johnsson et al. |
| 8,182,834 B2 | | 5/2012 | Johnsson et al. |
| 8,187,629 B2 | | 5/2012 | Barauskas et al. |
| 8,236,292 B2 | | 8/2012 | Thuresson et al. |
| 8,236,755 B2 | | 8/2012 | Thuresson et al. |
| 2002/0026027 A1 | | 2/2002 | Ansell |
| 2003/0022242 A1 | | 1/2003 | Anderson |
| 2004/0018241 A1 | | 1/2004 | Houze et al. |
| 2004/0201117 A1 | | 10/2004 | Anderson |
| 2005/0136059 A1 | | 6/2005 | Thorpe et al. |
| 2006/0073203 A1 | | 4/2006 | Ljusberg-Wahren et al. |
| 2007/0080323 A1 | | 4/2007 | Joabsson et al. |
| 2007/0110777 A1 | | 5/2007 | Joabsson et al. |
| 2007/0134336 A1 | | 6/2007 | Worle et al. |
| 2007/0231374 A1 | | 10/2007 | Tiberg et al. |
| 2008/0124394 A1 | | 5/2008 | Johnsson et al. |
| 2008/0146490 A1 | | 6/2008 | Joabsson et al. |
| 2008/0161276 A1 | | 7/2008 | Johnsson et al. |
| 2008/0214995 A1 | | 9/2008 | Boyd et al. |
| 2008/0274176 A1 | | 11/2008 | Johnsson et al. |
| 2009/0069221 A1 | * | 3/2009 | Joabsson et al. ............... 514/11 |
| 2009/0155193 A1 | | 6/2009 | Joabsson et al. |
| 2009/0170782 A1 | | 7/2009 | Joabsson et al. |
| 2011/0230569 A1 | | 9/2011 | Nistor et al. |

(Continued)

FOREIGN PATENT DOCUMENTS

| | | |
|---|---|---|
| EP | 1600162 | 11/2005 |
| WO | WO 1993/06921 A1 | 4/1993 |
| WO | WO 95/34287 A1 | 12/1995 |

(Continued)

OTHER PUBLICATIONS

Tiberg, "Camurus announces positive phase 1 results with its new long-acting octreotide product CAM2029", CAMURUS AB; Apr. 24, 2007; pp. 1-2.*
Tiberg et al., "Camurus receives positive opinion for orphan drug designation for CAM2029", CAMURUS AB; May 26, 2009; pp. 1-2.*
Tiberg et al., "Lipid Liquid Crystals for Prenteral Sustained-Release Applications: Combining Ease of Use and Manufacturing with Consistent Drug Release Control", obtained from www.ondrugdelivery.com on Dec. 27, 2014; 2010, pp. 9-13.*
Evaluate™."CAM2029", obtained from http://www.evaluategroup.com on Dec. 27, 2014.*

(Continued)

*Primary Examiner* — Lianko G Garyu
(74) *Attorney, Agent, or Firm* — J.A. Lindeman & Co., PLLC (57) ABSTRACT The present invention relates to formulation precursors (pre-formulations) for the in situ generation of compositions for the controlled release of the salts of peptide active agents, including somatostatin analogues. The invention also relates to pre-formulations of amphiphilic components and at least one salt of a peptide active agent (e.g., somatostatin analogue) for parenteral application.

21 Claims, 2 Drawing Sheets

(56) References Cited

U.S. PATENT DOCUMENTS

| | | |
|---|---|---|
| 2012/0028890 A1 | 2/2012 | Nistor et al. |
| 2012/0269772 A1 | 10/2012 | Thuresson et al. |

FOREIGN PATENT DOCUMENTS

| | | | |
|---|---|---|---|
| WO | WO 1997/13528 A1 | 4/1997 | |
| WO | WO 98/47487 A1 | 10/1998 | |
| WO | WO 02/02716 A2 | 1/2002 | |
| WO | WO 02/066014 A2 | 8/2002 | |
| WO | WO 02/068561 A2 | 9/2002 | |
| WO | WO 02/068562 A2 | 9/2002 | |
| WO | WO 03/002136 A2 | 1/2003 | |
| WO | WO 2003/057235 A2 | 7/2003 | |
| WO | WO 2004/087215 A1 | 10/2004 | |
| WO | WO 2005/014162 A1 | 2/2005 | |
| WO | WO 2005/021022 A2 | 3/2005 | |
| WO | WO 2005/046642 A1 | 5/2005 | |
| WO | WO 2005/048952 A2 | 6/2005 | |
| WO | WO 2005/063213 A1 | 7/2005 | |
| WO | WO 2005/070394 A2 | 8/2005 | |
| WO | 2005/117830 A1 | 12/2005 | |
| WO | 2006/075123 A1 | 7/2006 | |
| WO | 2006/075124 A1 | 7/2006 | |
| WO | WO 2006/075125 A1 | 7/2006 | |
| WO | WO 2006/077362 A1 | 7/2006 | |
| WO | WO 2006075124 A1 * | 7/2006 | ........... A61K 9/0019 |
| WO | WO 2006/131730 A1 | 12/2006 | |
| WO | WO 2008/152401 A1 | 12/2008 | |
| WO | WO 2009/024795 A1 | 2/2009 | |
| WO | WO 2009/024797 A1 | 2/2009 | |
| WO | WO 2010/020794 A1 | 2/2010 | |

OTHER PUBLICATIONS

Evaluate™, "Camurus Announces Positive Phase 1 Results With its New Long-acting Octreotide Product CAM2029", obtained from fromhttp://www.evaluategroup.com on Dec. 27, 2014; dated Apr. 24, 2007, pp. 1-2.*
Bianchi et al., The Role of pH, Temperature, Salt Type, and Salt Concentration on the Stability of the Crystalline, Helical, and Randomly Coiled Forms of Collagen, The Journal of Biological Chemistry, 1967, 1361-1369.*
von Hippel et al., Neutral Salts: The Generality of Their Effects on the Stability of Macromolecular Conformations, Science, 1964, 577-580.*
Martel et al., Enzyme Linked Immunosorbent Assay (ELISA) Method for the Determination of TH0318, a New GLP-1 Analogue in Development for Diabetes, Poster, 2005 (Year: 2005).*
Comets et al., "Nonparametric analysis of the absorption profile of octreotide in rabbits from long-acting release formulation OncoLAR," J. Controlled Release 59:197-205 (1999).
International Search Report of PCT/GB2008/002035 dated Oct. 6, 2008.
International Preliminary Report on Patentability of PCT/GB2008/002035 dated Dec. 17, 2009.
Written Opinion of the International Searching Authority of PCT/GB2008/002035 dated Dec. 15, 2009.
About Sandostatin: Proven Control of GH, 1GF-1 and Gastrointestinal Hormone, from www.sandostatin.com/about.sandostatin/index.html and linked documents.
"Acromegaly" from www.niddk.nil.gov/health/endo/pubs/acro/acro.htm.
American Peptide Company, Product Details "Somatostatin and analogs," from www.americanpeptide.com/.
N. Ardjomand et al., "Expression of Somatostatin Receptors in uveal melanomas," Inv. Opthalmol. & Vis. Sci., 2003, vol. 44, No. 3, pp. 980-987.
Barauskas et al., Pharmaceutical Nanotechnology, "Interactions of lipid-based liquid crystalline nanoparticles with model and cell membranes," International Journal of Pharmaceutics 391 (2010) pp. 284-291.
R. Berges, "Eligard: Pharmacokinetics, Effect on Testosterone and PSA Levels and Tolerability," European Urology Supplements, 2005, vol. 4, pp. 20-25.
Chang, J., "Use of GnRH agonists in the treatment of hyperandrogenism and hirsutism," print out from http://patients.uptodate.com.
P. Chanson et al., "Comparison of octreotide acetate LAR and lanreptide SR in patients with acromegaly," Clin. Endocrinology, 2001, vol. 54, No. 1, pp. 11-13, (Abstract only).
F. Dall'Antonia, "Structure determination of organo-silicon compounds.", pp. 6 to 8 from http://shelx.uni-ac.gwdg.de/-fabio/endwkcon.htm.
Definition of analog from http://cancerweb.ncl.ac.uklomd/about.html, pp. 1-5. Accessed Jul. 7, 2005.
B. L. Erstad, "Octreotide for acute variceal bleeding," Ann. Pharmacother., 2001, vol. 35, No. 5, pp. 618-626. (Abstract only).
FDA's 510(k) Summary of Camurus AB, episil® K101769.
A. K. Flogstad et al., "Sandostatin LAR in acromegalic patients: long term treatment," J. Clinical Endocrinology & Metabolism, 1997, vol. 82, No. 1, pp. 23-28.
P. R. Gibson & J. G. Muir, "Reinforcing the mucus: a new therapeutic approach for ulcerative colitis," Gut, 2005, vol. 54, pp. 900-903.
L. M. Grant & F. Tibert, "Normal and Lateral Forces between Lipid Covered Solids in Solution: Correlation with Layer Packing and Structure," Biophysical Journal, 2002, vol. 82, pp. 1373-1385.
B.A. Hills, "Surface-active phospholipid: a Pandora's box of clinical applications. Part II. Barrier and lubricating properties," Internal Medicine Journal, 2002, vol. 32, pp. 242-251.
G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.
H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.
Indications and Usage of Eligard, pp. 1-5, print out from http:ffw-ww.rxlist.com, 2003.
Information About Buprenorphine Therapy, print out from http://buprenorphine.samhsa.gov/about.html, pp. 1-4, no date.
Information on Goserelin Acetate print out form http://www.bachem.com/, no date.
Information on Goserelin Subcutaneous, Monograph—Goserelin Acetate, pp. 1-7, print out form www.medscape.com, 2005.
Information on Leuprolide Intramuscular, Monograph—Leuprolide Acetate, pp. 1-20, print out for www.medscape.com, 2005.
Information on Leuprolide (3 Month) Intramuscular, Monograph—Leuprolide Acetate, pp. 1-20, print out from www.medscape.com, 2005.
Invitrogen, "Pluronic F-127," Molecular Probes Invitrogen Detection Technologies, pp. 1-2, 2008.
Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.
Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.
Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.
J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).
L. M. Knudsen, "Glucagon-like Peptide-1: The Basis of a New Class of Treatment for Type 2 Diabetes," J. Med. Chem. (2004), vol. 47, pp. 4128-4134.

(56) References Cited

OTHER PUBLICATIONS

L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.
I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.
"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.
MSDS for Ethylene Glycol and Abbreviations used in Toxicity data.
Novartis Pharmaceuticals Corporation, "Sansdostatin LAR Depot (octreotide acetate for injectable suspension)", pp. 1-19.
PDR Information on Eligard 30 mg (Sanofi-Synthelabo), print out from www.Drugs.com, pp. 1-14, 2004.
Pharmaceutical Information on Lupron Depot, print out from www.rxmed.com, pp. 1-8, no date.
Product Specification of Leuprolide by GL Biochem, print out from http://www.glschina.com, 2005.
Published Data Provided by Sandostatin LAR "The Latest Research and Treatment Information for Pituitary Disorders" from http://www.sandostatin.com/published data/index.html, 2005.
O. Sartor "Eligard: Leuprolide Acetate in a Novel Sustained-Release Delivery System," Urology, 2003, vol. 61, (Supplement 2A), pp. 25-31.
K. J. Schuh et al., "Onset, magnitude and duration of opioid blockade produced by buprenorphine and naltrexone in humans," Psychopharmacology, (Berl), Jul. 1999, vol. 145, No. 2, pp. 162-174 (Abstract only).
J. C. Shah et al., "Cubic phase gels as drug delivery systems," Advanced Drug Delivery Reviews, 2001, vol. 47, pp. 229-250.
"Setting new standards of care," Mixing and Administration instructions for Sandostatin LAR, 2003.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Drug delivery applications of non-lamellar liquid crystalline phases and nanoparticles", J. Drug Del Sci. Tech., 21(1) pp. 101-109, 2011.
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Treating Acromegaly, from http://www.sandostatin.com/lreating acromegaly/index.html and linked documents, 2005.
Welin et al., "High-dose treatment with a long-acting somatostatin analogue in patients with advanced midgut carcinoid tumours," 2004, Society of the European Journal of Endocrinology, vol. 151, pp. 107-112.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.
Apr. 23, 2014, Office Action in U.S. Appl. No. 11/795,243.
Martel et al., "Enzyme Linked Immunosorbent Assay (ELISA) Method for the Determination of TH0318, a New GLP-1 Analogue in Development for Diabetes," Poster, 2005.
Product Information on Zoladex Goserelin Acetate Implant (Equivalent to 10.8 mg goserelin). revised Oct. 2010.
Product Information on Zoladex Goserelin Acetate Implant (Equivalent to 10.8 mg goserelin), revised Feb. 2016.

* cited by examiner

Figure 1. Decrease in viscosity at 25 °C of the depot precursor on addition of solvents. PC/GDO (5/5) is a precursor to a reversed hexagonal $H_{II}$ phase and PC/GDO (4/6) is a precursor to a reversed cubic $I_2$ phase.

Figure 2. In vitro release of octreotide (octreotide base (OCT(0)) from formulation #186 containing octreotide acetate (OCT(Ac)) and from formulation #183 containing octreotide chloride (OCT(Cl)). The release was measured after 24 h at 37°C at different formulation-to-PBS weight ratios. Error bars represent standard deviation (n ≥ 2).

Figure 3. Octreotide content (expressed as % of nominal content) as a function of storage time and temperature. Note the dramatic stability enhancing effect of changing the counter-ion from acetate (formulation #174) to chloride (formulation #192).

Figure 4. Breakdown products detected by HPLC and expressed as % total area of the peaks detected at 215 nm for formulations containing octreotide acetate (#174) and octreotide chloride (#192). Note the dramatic stability enhancing effect of changing the counter-ion from acetate (formulation #174) to chloride (formulation #192).

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: SST-14
<220> FEATURE:
<221> NAME/KEY: DISULFID
<222> LOCATION: (3)..(14)

<400> SEQUENCE: 1

Ala Gly Cys Lys Asn Phe Phe Trp Lys Thr Phe Thr Ser Cys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Octreotide
<220> FEATURE:
<221> NAME/KEY: DISULFID
<222> LOCATION: (2)..(7)
<220> FEATURE:
<221> NAME/KEY: MOD_RES
<222> LOCATION: (8)..(8)
<223> OTHER INFORMATION: X = THR-OL
```

```
<400> SEQUENCE: 2

Phe Cys Phe Trp Lys Thr Cys Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: LANREOTIDE
<220> FEATURE:
<221> NAME/KEY: MOD_RES
<222> LOCATION: (1)..(1)
<223> OTHER INFORMATION: X = NH2-NAPH
<220> FEATURE:
<221> NAME/KEY: DISULFID
<222> LOCATION: (2)..(7)
<220> FEATURE:
<221> NAME/KEY: MOD_RES
<222> LOCATION: (8)..(8)
<223> OTHER INFORMATION: X = THR-CONH2

<400> SEQUENCE: 3

Xaa Cys Tyr Trp Lys Val Cys Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: CYCLIC LANREOTIDE
<220> FEATURE:
<221> NAME/KEY: MOD_RES
<222> LOCATION: (1)..(1)
<223> OTHER INFORMATION: X = NH2-NAPH
<220> FEATURE:
<221> NAME/KEY: DISULFID
<222> LOCATION: (2)..(7)
<220> FEATURE:
<221> NAME/KEY: MOD_RES
<222> LOCATION: (8)..(8)
<223> OTHER INFORMATION: X = THR-CONH2

<400> SEQUENCE: 4

Xaa Cys Tyr Phe Lys Val Cys Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: SOM230
<220> FEATURE:
<221> NAME/KEY: MOD_RES
<222> LOCATION: (1)..(1)
<223> OTHER INFORMATION: X = PRO(2-AMINOETHYL-CARBAMATE)
<220> FEATURE:
<221> NAME/KEY: MOD_RES
<222> LOCATION: (2)..(2)
<223> OTHER INFORMATION: X = GLY(PHENYL)
<220> FEATURE:
<221> NAME/KEY: MOD_RES
<222> LOCATION: (5)..(5)
<223> OTHER INFORMATION: X = TYR(METHYLPHENYL)

<400> SEQUENCE: 5

Xaa Xaa Trp Lys Xaa Phe
1               5
```

PEPTIDE SLOW-RELEASE FORMULATIONS

This is a National Phase Application in the United States of International Patent Application No. PCT/GB2008/002035 filed Jun. 13, 2008, which claims priority to Great Britain Patent Application No. 0711656.9 filed Jun. 15, 2007.

SEQUENCE LISTING

The instant application contains a Sequence Listing which has been submitted in ASCII format via EFS-Web and is hereby incorporated by reference in its entirety. Said ASCII copy, created on Aug. 7, 2013, is named 94992-12_ST25.txt and is 1846 bytes in size.

The present invention relates to formulation precursors (pre-formulations) for the in situ generation compositions for the controlled release of the salts of peptide active agents, especially of somatostatin analogues. In particular, the invention relates to pre-formulations of amphiphilic components and at least one salt of a peptide active agent (e.g. somatostatin analogue) for parenteral application.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable since self-administration may be difficult and thus cause inconvenience and/or poor compliance. In such cases it would be advantageous for a single administration must provide active agent at a therapeutic level over the whole period during which activity is needed. Peptide active agents are particularly suitable for formulation as sustained release compositions because naturally occurring peptidase activity typically results in a short half-life for these actives.

Somatostatins (Growth Hormone Release Inhibiting Factors, SSTs) are natural peptide hormones with a wide distribution in animals, acting as neurotransmitters in the central nervous system, and having diverse paracrine/autocrine regulatory effects on several tissues. Two biologically active products are known in higher species, SST-14 and SST-28, a congener of SST-14 extended at the N-terminus. SST-14 is a 14 residue cyclic peptide hormone having the sequence Ala-Gly-Cys-Lys-Asn-Phe-Phe-Trp-Lys-Thr-Phe-Thr-Ser-Cys (SEQ ID NO: 1), where the two cysteine residues are connected by a disulphide bridge to generate a type II β-turn at the key binding sequence of Phe-Trp-Lys-Thr. The biological half-life of natural SST-14 is very short (1-3 minutes) and so it is not, in itself, a viable therapeutic in current formulations, but an increasing number of somatostatin analogues are becoming available with higher activities and/or longer clearance times in vivo.

Somatostatin analogues, such as octreotide, lanreotide, vapreotide, pasireotide (SOM 230) and related peptides, are used or indicated in the treatment of a variety of conditions where they are typically administered over an extended period.

Octreotide, for example, is the synthetic octapeptide with sequence D-Phe-Cys-Phe-D-Trp-Lys-Thr-Cys-Thr-ol (2-7 disulphide bridge) (SEQ ID NO: 2) and is typically administered as an acetate salt. This SST-14 derivative retains the key Phe-(D)Trp-Lys-Thr β-turn required for in vivo SST-like activity but, in contrast to the natural hormone, has a terminal half-life of around 1.7 hours. Octreotide is used in treatment of conditions including carcinoid tumours and acromegaly, and is typically administered over a sustained period of weeks, or more commonly many months or years. Somatostatin analogues are of particular interest for the treatment of many different types of cancers since a wide variety of tumours are found to express somatostatin receptors (SSTRs). There are five known types of SSTRs (SSTR1-SSTR5), showing equally high affinity for SST-14. The most investigated somatostatin analogues, including octreotide, show high selectivity for SSTR2 and SSTR5; thus, octreotide is of particular interest for the treatment of tumours expressing these types of receptors.

The most common "simple" formulation of Octreotide is "SANDOSTATIN®" (RTM) from Novartis. This is an aqueous solution for subcutaneous (s.c) injection, and a 100 μg dose reaches a peak concentration of 5.2 ng/ml at 0.4 hours post injection. The duration of action can be up to 12 hours but s.c. dosing is generally carried out every 8 hours. Evidently, s.c. injection 3 times daily for periods of months or years is not an ideal dosing regime.

In order to avoid the need for multiple daily injections of octreotide, a further formulation is available; "SANDOSTATIN LAR" ®, again from Novartis. This is a formulation of octreotide in poly lactic co-glycolic acid microspheres which, after resuspension, may be administered by intra muscular (i.m.) injection.

All of the known commercially available somatostatin analogue preparations, especially those having delayed release are formulated with the peptide active in the form of the acetate salt.

Carcinoid tumours are intestinal tumour arising from specialised cells with paracrine functions (APUD cells). The primary tumour is commonly developed in the appendix, where it is clinically benign. Secondary, metastatic, intestinal carcinoid tumours secrete excessive amounts of vasoactive substances, including serotonin, histamine, prostaglandins, and polypeptide hormones. The clinical result is carcinoid syndrome (a syndrome of episodic cutaneous flushing, cyanosis, abdominal cramps, and diarrhoea in a patient with valvular heart disease and, less commonly, asthma and arthropathy). Carcinoid tumours may grow anywhere in the gastrointestinal tract (and in the lungs) with approximately 90% originating in the appendix. The remainder occur in the ileum, stomach, colon or rectum.

Currently, treatment of carcinoid syndrome starts with i.v. bolus injection followed by i.v. infusion of SANDOSTATIN®. When sufficient effect on symptoms has been established, treatment with a depot formulation of octreotide formulated in poly lactic-co-glycolic acid (PLGA) microspheres is started. However, during the first two weeks or more after injection of the depot, daily s.c. injections with SANDOSTATIN® are recommended to compensate for the slow release from the PLGA spheres.

Acromegaly is a rare chronic and insidious hormonal disorder that occurs when the pituitary gland produces excess growth hormone (GH). It most commonly affects middle-aged adults and may lead to premature death. Diabetes mellitus, hypertension, and increased risk of cardiovascular disease are the most serious health consequences of acromegaly. In addition, patients with acromegaly are at an increased risk of developing colon polyps, which can become cancerous. The prevalence of acromegaly is approximately 60 cases per million population, and the incidence is 3.3 new cases per million per year. The word acromegaly comes from the Greek words for "extremities" (acro) and "great" (megaly), because one of the most common symptoms of this condition is abnormal growth of the hands and feet.

Acromegaly is caused by prolonged overproduction of growth hormone (GH) and excessive production of insulin-like growth factor-I (IGF-I). In 98 percent of oases, the overproduction of GH is caused by a pituitary adenoma. The rate of GH production and the aggressiveness of the tumour vary from patient to patient. Generally, more aggressive tumours are seen in younger patients.

Treatment of acromegaly is initiated by a period of s.c. injections three times per day (optimal daily dose=300 μg octreotide). After the last s.c. dose, and providing a suitable effect is observed, the treatment with a depot formulation of octreotide formulated in poly lactic-co-glycolic acid (PLGA) microspheres is started. Dose adjustments are made after measurement of biomarkers (GH and IGF-1), typically after around 3 months.

The existing octreotide slow release formulation relies upon a well-established in vivo degrading-polymer type of depot formulation. This is typically a biodegradable polymer containing poly (lactic acid) (PLA) and/or poly (lactic-co-glycolic acid) (PLGA) and may be in the form of a solution in an organic solvent, a pre-polymer mixed with an initiator, encapsulated polymer particles or (as in the case of octreotide) polymer microspheres.

The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microsphere formulation). The local irritation caused by the lactic and/or glycolic acid which is released at the injection site is also a noticeable drawback. There is also often quite a complex procedure to prepare the injection dose from the powder precursor.

One highly significant drawback of the known PLGA octreotide depot system is the complexity of preparation for the administering person. The depot is provided as a powder precursor of the octreotide-containing microspheres, plus a diluent in which these must be uniformly suspended. Successful preparation of the depot system for administration requires a multi-step method which must be followed precisely in order to ensure that the powder-precursor is completely saturated and in a uniform suspension prior to injection. The depot system must then be administered immediately by a method involving continual rocking of the syringe to maintain a uniform dispersion up to the point of deep gluteal intramuscular injection.

Although simple preparation is a highly advantageous feature, this must often be weighed against the need for stability to long term storage. Previously known octreotide depot compositions such as those based upon PLGA or even previously known lipid-depot compositions (e.g. WO2006/075124) are not generally stable to long-term storage, especially at room temperature or higher. Evidently, it would be an advantage to provide compositions which not only avoided the need for complex preparation, but could also be stored in ready-to-use form for extended periods, especially at room temperature.

A further limitation of the existing PLGA octreotide depot systems is that dosing cannot easily be tailored to suit particular patients. It has recently been proposed that dosing of somatostatin analogues should be administered relative to the body weight of the subject since plasma concentrations have shown a marked variability by subject weight. A depot system comprising a pre-weighted dry powder which is suspended unstably in an injection vehicle does not allow any such control, however, unless a considerable range of pre-measured doses is to be provided. The suspension cannot be partially administered because the particles are not evenly suspended. It would thus be a considerable advantage to have a homogeneous depot precursor which allowed administration of a dose to be decided on a subject-specific basis at the time of administration.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

In the case of octreotide, the functional window ranges from around 0.8 to 20+ ng/ml, but even so, as indicated above, the use of PLGA microspheres causes a lag of several weeks during which "top-up" injections must be provided. Evidently, it would be an advantage to provide a depot system which achieved a "plateau" level more quickly. The release of octreotide into rabbits from a PLGA microsphere product was studied by Comets et al. (J. Controlled Release 59 (1999) 197-05), for example, and this indicated the "third phase" release of over 85% of the active agent began more than 15 days after administration.

The low loading capacity of polymeric depot products, as well as the nature of microparticles causes additional problems in administration. In particular, a relatively high volume, of around 5 ml must be injected in order to carry the microparticle suspension, and the suspension can easily block syringe needles (hence the need for adherence to strict administration protocols), thus requiring that a relatively wide (e.g. 19-gauge) needle be used. Both of these factors, as well as the need for deep i.m. injection, result in considerable discomfort to the patient during administration. It would be a considerable advantage if a depot system could be provided requiring lower volumes of administration, which was administrable through a narrower gauge needle, and/or did not require such deep injections.

The manufacture of PLGA microbeads is additionally a considerable difficulty with existing somatostatin analogue depot systems. In particular, since the beads are particulate, they cannot be sterile-filtered and furthermore, since the PLGA copolymer melts at around 40° C., they cannot be heat-treated for sterility. As a result, a complex manufacturing process must all be conducted under conditions of high sterility.

Even though known lipid depot compositions of somatostatin analogues overcome many of the problems associated with prior-known depot compositions, it remains desirable to provide further control over the dosing and release rate. As indicated above, octreotide and other somatostatin analogues may be required at stable dosage levels over long periods, and thus it is of advantage to provide compositions which will release active agent at an even more carefully controlled rate and for an even further extended duration.

The present inventors have now established that slow-release compositions of peptide actives, especially somatostatin analogues are surprisingly more effective if an appropriate counter-ion is chosen for the salt of the peptide active.

In a first aspect, the present invention thus provides a composition for the delayed delivery of a peptide active agent comprising;
i) a salt of said peptide active agent comprising at least one positively charged peptide ion and at least one negatively charged counter-ion
ii) a sustained-release delivery vehicle.

Wherein said at least one negatively charged counter-ion is a halide ion, preferably a chloride or bromide ion.

Many sustained-release delivery systems exist, and many of these are appropriate for use in the present invention. For example, polymer-based slow-release compositions based upon degradable polymers such as PLGA, poly-lactate or polyglycolate are suitable, but most suitable for use in the present invention are lipid-based depot compositions, such as those described in WO2005/117830 and/or WO2006/075124, the complete disclosures of which, along with the disclosures of all documents cited herein, being hereby incorporated by reference. The formulation of active agents into biodegradable polymer depot formulations is now well established and well known in the art, and the peptide salts of the present invention may thus be formulated with these using known methods.

Preferably, the composition of the present invention is capable of releasing octreotide at a functional concentration for at least 1 month. Further preferably, the composition is stable to storage at 25 degrees Celsius or higher for at least 4 weeks without loss of more than 5% or the original activity of the active agent. Preferred peptide active agents are somatostatin analogues as described herein.

In one preferred aspect of the invention, the composition of the invention is formed by injection of a low-viscosity lipid composition which subsequently undergoes a phase-change whereby to form a slow-release composition. In this aspect, the invention provides a pre-formulation comprising a low viscosity mixture of:
a) at least one diacyl glycerol;
b) at least one phosphatidyl choline;
c) at least one oxygen containing organic solvent;
d) a salt of at least one somatostatin analogue comprising at least one positively charged peptide ion and at least one negatively charged counter-ion wherein the pre-formulation forms, or is capable of forming, at least one liquid crystalline phase structure upon contact with an aqueous fluid and wherein said at least one negatively charged counter-ion is a halide ion, preferably a chloride or bromide ion.

Generally, the said aqueous fluid will be a body fluid particularly extra-vascular fluid, extracellular fluid/interstitial fluid or plasma, and the pre-formulation will form a liquid crystalline phase structure when contacted with such a fluid (e.g. in vivo). The pre-formulation of the invention will generally not contain any significant quantity of water prior to administration.

Preferably the pre-formulation will be in a form suitable for administration (i.e. without requiring preparation steps which alter the composition, such as dilution or suspension). It is furthermore preferable that the pre-formulation (especially where it is in a form suitable for administration) is stable to storage at room temperature for at least 1 month, preferably at least 6 months without loss of more than 10%, preferably 5% of the activity of the active agent before storage.

In a further aspect of the invention, there is also provided a method of delivery of a somatostatin analogue to a human or non-human animal (preferably mammalian) body, this method comprising parenterally administering (e.g. i.m. or preferably s.c.) a pre-formulation comprising a low viscosity mixture of:
a) at least one diacyl glycerol;
b) at least one phosphatidyl choline;
c) at least one oxygen containing organic solvent;
d) a salt of at least one somatostatin analogue comprising at least one positively charged peptide ion and at least one negatively charged counter-ion;
whereby to form at least one liquid crystalline phase structure upon contact with an aqueous fluid in vivo following administration and wherein said at least one negatively charged counter-ion is a halide ion, preferably a chloride or bromide ion. Preferably, the pre-formulation administered in such a method is a pre-formulation of the invention as described herein.

In a further aspect, the present invention also provides a method for the preparation of a liquid crystalline depot composition comprising exposing a pre-formulation comprising a low viscosity mixture of:
a) at least one diacyl glycerol;
b) at least one phosphatidyl choline;
c) at least one oxygen containing organic solvent; and
d) a salt of at least one somatostatin analogue comprising at least one positively charged peptide ion and at least one negatively charged counter-ion;
to an aqueous fluid in vivo;
wherein said at least one negatively charged counter-ion is a halide ion, preferably a chloride or bromide ion.

Preferably the pre-formulation administered is a pre-formulation of the present invention as described herein.

In a still further aspect the present invention provides a process for the formation of a pre-formulation suitable for the administration of a bioactive agent to a (preferably mammalian) subject, said process comprising forming a low viscosity mixture of
a) at least one diacyl glycerol;
b) at least one phosphatidyl choline;
c) at least one oxygen containing organic solvent;
and dissolving or dispersing a salt of at least one somatostatin analogue comprising at least one positively charged peptide ion and at least one negatively charged counter-ion in the low viscosity mixture, or in at least one of components a, b or c prior to forming the low viscosity mixture, wherein said at least one negatively charged counter-ion is a halide ion, preferably a chloride or bromide ion. Preferably the pre-formulation so-formed is a formulation of the invention as described herein.

In a yet still further aspect the present invention provides the use of a low viscosity mixture of
a) at least one diacyl glycerol;
b) at least one phosphatidyl choline;
c) at least one oxygen containing organic solvent;
d) a salt of at least one somatostatin analogue comprising at least one positively charged peptide ion and at least one negatively charged counter-ion;
in the manufacture of a pre-formulation for use in the sustained administration of said somatostatin analogue, wherein said pre-formulation is capable of forming at least one liquid crystalline phase structure upon contact with an aqueous fluid and wherein said at least one negatively charged counter-ion is a halide ion, preferably a chloride or bromide ion.

In a still further aspect, the present invention provides a method for the treatment of a human or non-human mammalian subject in need thereof with a somatostatin analogue, said method comprising administering to said subject a pre-formulation comprising a low-viscosity mixture of
a) at least one diacyl glycerol;
b) at least one phosphatidyl choline;
c) at least one oxygen containing organic solvent;
d) a salt of at least one somatostatin analogue comprising at least one positively charged peptide ion and at least one negatively charged counter-ion;
wherein said at least one negatively charged counter-ion is a halide ion, preferably a chloride or bromide ion.

Preferably, the method of treatment is a method for the treatment of at least one condition selected from acromegaly, cancers (such as carcinomas and melanomas, tumours expressing at least one somatostatin receptor, SSTR2-positive tumours, SSTR-5-positive tumours, prostate cancers, gastro-entero-pancreatic neuroendocrine (GEP NE) tumours and especially carcinoid tumours, insulinomas, gastrinomas, vasoactive intestinal peptide (VIP)-producing tumours and glucagonomas), elevated growth hormone (GH), elevated IGF-I, varicial bleeding (especially esophageal), chemotherapy induced gastro intestinal problems (such as diarrhea), lymphorrhea, diabetic retinopathy, thyroid eye disease, obesity, pancreatitis, and related conditions.

In a yet further aspect, the present invention provides the use of;
a) at least one diacyl glycerol;
b) at least one phosphatidyl choline;
c) at least one oxygen containing organic solvent;
d) at a salt of at least one somatostatin analogue comprising at least one positively charged peptide ion and at least one negatively charged counter-ion;
in the manufacture of a low viscosity pre-formulation medicament for use in the in vivo formation of a depot for treatment of acromegaly, cancer (such as carcinomas and melanomas, tumours expressing at least one somatostatin receptor, SSTR2-positive tumours, SSTR-5-positive tumours, prostate cancers, GEP NE tumours and especially carcinoid tumours, insulinomas, gastrinomas, VIP-producing tumours and glucagonomas), elevated GH, elevated IGF-I, varicial bleeding (especially espohageal), chemotherapy induced gastro intestinal problems (such as diarrhea), lymphorrhea, diabetic retinopathy, thyroid eye disease, obesity, pancreatitis, and/or related conditions wherein said at least one negatively charged counter-ion is a halide ion, preferably a chloride or bromide ion.

The pre-formulations of the present invention are highly advantageous in that they are stable to prolonged storage in their final "administration ready" form. As a result, they may readily be supplied for administration either by health professionals or by patients or their careers, who need not be fully trained health professionals and may not have the experience or skills to make up complex preparations. It is the surprising finding of the inventors that compositions wherein the peptide active is in the form of a salt with the specified counter-ions (as described herein) are significantly more stable even than the relatively stable compositions described in WO2006/075124 having acetate counter-ions.

In a yet further aspect, the present invention provides a disposable administration device (which is also to include a device component) pre-loaded with a measured dose of a preformulation of the present invention. Such a device will typically contain a single dose ready for administration and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

In an additional aspect, the present invention thus provides a disposable administration device pre-loaded with a measured dose of a preformulation comprising a low viscosity mixture of:
a) at least one diacyl glycerol;
b) at least one phosphatidyl choline;
c) at least one oxygen containing organic solvent;
d) a salt of at least one somatostatin analogue comprising at least one positively charged peptide ion and at least one negatively charged counter-ion;
(especially wherein the pre-formulation forms, or is capable of forming, at least one liquid crystalline phase structure upon contact with an aqueous fluid) wherein said at least one negatively charged counter-ion is a halide ion, preferably a chloride or bromide ion.

The pre-filled devices of the invention may also suitably be included in an administration kit, which kit also forms a further aspect of the invention. In a still further aspect, the invention thus provides a kit for the administration of at least one somatostatin analogue, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as describe herein and/or for the treatment of a disease indicated herein above.

In a yet further aspect, the invention thus additionally provides kit for the administration of at least one somatostatin analogue, said kit containing a measured dose of a formulation comprising a low viscosity mixture of:
a) at least one diacyl glycerol;
b) at least one phosphatidyl choline;
c) at least one oxygen containing organic solvent; and
d) a salt of at least one somatostatin analogue comprising at least one positively charged peptide ion and at least one negatively charged counter-ion;
(especially wherein the pre-formulation forms, or is capable of forming, at least one liquid crystalline phase structure upon contact with an aqueous fluid) wherein said at least one negatively charged counter-ion is a halide ion, preferably a chloride or bromide ion.

Although the present invention is applicable to all types of slow-release compositions (e.g. those requiring dosing no more frequently than every 7 days), certain formulations of the present invention generate a non-lamellar liquid crystalline phase following administration. The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

Where they form liquid crystalline depot compositions after administration, it is important that the pre-formulations of the invention are not liquid crystalline prior to administration because bulk liquid crystalline phase is generally highly viscous. These pre-formulations are thus low viscosity, non-liquid-crystalline formulations which undergo a phase change upon administration to form a liquid crystalline mass. Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 min syringe filter. A typical range of suitable viscosities would be, for example, 0.1 to 5000 mPas, preferably 1 to 1000 mPas at 20° C.

Figure 1:
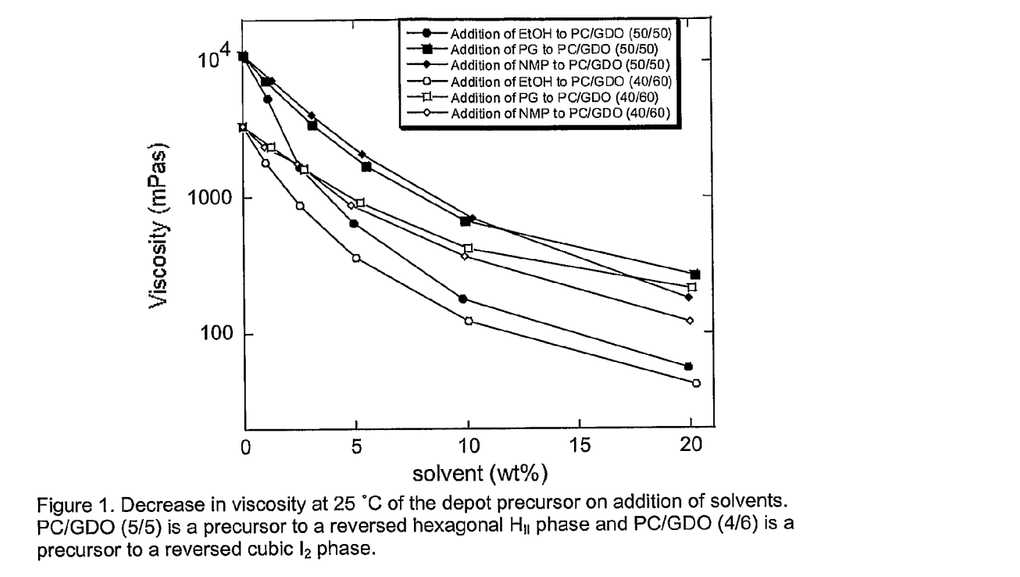
FIG. 1 demonstrates the non-linear decrease of preformulation viscosity upon addition of N-methylpyrrolidinone (NMP) and EtOH.

It has been observed that by the addition of small amounts of low viscosity solvent, as indicated herein, a very significant change in viscosity can be provided. As indicated in FIG. 1, for example, the addition of only 5% solvent to a lipid mixture can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

The present invention provides a pre-formulation comprising components a, b, c and at least one peptide salt, such as a salt of a somatostatin analogue as indicated herein. The amounts of these components will typically be in the range 40-70% a), 30-60% b) and 0.1-20% c), with the peptide salt present at 0.1% to 10%. All % being by weight herein throughout, unless otherwise indicated. The formulations may consist of essentially only these components and in one aspect consist entirely of such components. Preferable ranges for component a) are 43-60%, particularly 45-55 and preferable ranges of component b) are 35-55%, particularly 40 to 50%. The preferred range for component c) is 0.1 to 10%. These and all preferable aspects of the invention may be used individually or in any combination, unless specifically indicated otherwise.

Ratios of a:b are typically 40:60 to 70:30, preferably 45:55 to 60:40 and more preferably 48:52 to 55:45. Ratios of around 50:50 are highly effective.

The amount of solvent component c) in a preformulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 20% solvent will provide suitable release and viscosity properties. This will preferably be 0.1 to 10%, more preferably 2 to 8% and an amount of around 5% is highly effective.

It is the remarkable finding of the present inventors that the proportion of solvent in the formulation can be used to "tune" the release profile of the active agent during the first few days of release. In particular, although all formulations of the invention have a surprisingly low "burst/lag" effect (in fact there may be no lag period at all), and reach a plateau release level within a few days (e.g. 5 days, preferably 3 days, more preferably 1 day) of injection, if a controlled "burst"/initial release of active agent is required in the first 1-2 days then this can be provided by increasing the solvent proportion to the upper region of the range given above. In contrast, in the mid- to lower-region of the range, a formulation giving a depot with essentially no burst and a rapid decline to the plateau release level is provided.

Thus, in one embodiment, the present invention provides formulations and depots containing around 0.1 to 6 wt % component c) and having a low release of the active compound during the first days after administration ("low-burst profile"). In an alternative embodiment, the present invention provides formulations and depots containing around 6.5 to 10 wt % component c) and having high initial release of the active compound during the first days after administration ("burst profile").

The low initial release ("low-burst profile") of active agent is defined such that the area under a plasma concentration against time the curve during the first 24 hours is less than 15% of the area under the curve for the entire curve (measured or extrapolated from time 0 to infinity or from time 0 to the last sampling time point), more preferably less than 10% and most preferable less than 7%. In addition, the decline to plateau plasma concentration levels after the initial peak should be rapid, such that plateau is reached with in 48 hours, more preferably within 24 hours, and most preferably within 12 hours. Conversely, a high initial release ("burst profile") is such that more than 15% of active agent is released within 24 hours and more preferably more than 20% is released during the first 24 hours. The decline to plateau will not occur until after 36 hours, more preferably after 48 hours and most preferably after 72 hours. It is preferable that each of these profiles is combined with a rapid settling of the plasma active agent concentration to "plateau" level. For example, the plasma concentration after 10 days should be no more than 50% greater or less than the average concentration over days 5 to 20. Preferably this will be no more than 30% and more preferably no more than 20%.

As indicated above, the amount of component c) in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein.

Component "a" as indicated herein is at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a. Preferably this component will include at least a portion of glycerol dioleate (GDO). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component "b" in the present invention is at least one phosphatidyl choline (PC). As with component a, this component comprises a polar head group and at least one non-polar tail group. The difference between components a and b lies principally in the polar group. The non-polar portions may thus suitably be derived from the fatty acids or corresponding alcohols considered above for component a. As with component a), the PC will contain two non-polar groups.

The phosphatidyl choline portion, even more suitably than any diacyl glycerol portion, may be derived from a natural source. Suitable sources of phospholipids include egg, heart, brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC are highly suitable. The PC component preferably contains at least 50% soy PC, more preferably at least 75% soy PC and most preferably essentially pure soy PC.

Since the pre-formulations of the invention are to be administered to a subject for the controlled release of a somatostatin analogue active agent, it is important that the components are biocompatible. In this regard, the preformulations of the present invention are highly advantageous since both PC and DAGs are well tolerated and are broken down in vivo into components that are naturally present in the mammalian body.

A particularly favoured combination of components a and b are GDO with PC, especially GDO with soy PC.

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the composition comprising a and b, i.e. preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water, or glycerol.

Typical solvents suitable for use as component c include at least one solvent selected from alcohols, ketones, esters (including lactones), ethers, amides and sulphoxides. Alcohols are particularly suitable and form the preferred class of solvents. Examples of suitable alcohols include ethanol, isopropanol and glycerol formal. Ethanol is most preferred. Monools are preferred to diols and polyols. Where diols or polyols are used, this is preferably in combination with an at least equal amount of monool or other preferred solvent. Examples of ketones include acetone and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides and sulphoxides include n-methylpyrrolidone (NMP), 2-pyrrolidone, dimethylacetamide (DMA) and dimethylsulphoxide (DMSO), respectively.

A highly preferred combination is soy PC, GDO and ethanol. This is especially compatible with the chloride or bromide of a somatostatin analogue, such as octreotide chloride. Compositions around 40-60% PC, 40-60% GDO, 3-10% Ethanol and 1 to 8% Octreotide chloride are preferred examples.

It is preferable that little or none of component c contains halogen substituted hydrocarbons since these tend to have lower biocompatibility. Where a portion of halogenated solvent such as dichloromethane or chloroform is necessary, this proportion will generally be minimised.

Component c as used herein may be a single solvent or a mixture of suitable solvents but will generally be of low viscosity. This is important because one of the key aspects of the present invention is that it provides preformulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

A further advantage of the present pre-formulations is that a higher level of bioactive agent may be incorporated into the system. In particular, by appropriate choice of components a-c (especially c), high levels of active agent may be dissolved or suspended in the pre-formulations. This allows a reduction in the administered volume and thus less discomfort to subjects.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

Certain of the pre-formulations of the present invention contain salts of one or more somatostatin analogues (which are preferred examples of the peptide actives, which in turn are intended by any reference to "active agents" herein). Since SST-14 is a peptide hormone, typical somatostatin analogues will be peptides, especially of 14 or fewer amino acids. Preferably such peptides will be structurally constrained such as by being cyclic and/or having at least one intra-molecular cross-link. Amide, ester or particularly disulphide crosslinks are highly suitable. Preferred constrained peptides will exhibit a type-2 β turn. Such a turn is present in the key region of somatostatin. Peptides may contain only amino acids selected from those 20 α-amino acids indicated in the genetic code, or more preferably may contain their isomers and other natural and non-natural amino acids, (generally α, β or γ, L- or D-amino acids) and their analogues and derivatives. The term "somatostatin analogue" as used herein may optionally also encompass SST-14 and/or SST-28, since these are viable peptide actives when formulated as salts in the very high performance slow-release formulations described herein.

Amino acid derivatives and amino acids not normally used for protein synthesis are especially useful at the termini of the peptides, where the terminal amino or carboxylate group may be substituted by or with any other functional group such as hydroxy, alkoxy, ester, amide, thio, amino, alkyl amino, di- or tri-alkyl amino, alkyl (by which is meant, herein throughout $C_1$-$C_{12}$ alkyl, preferably $C_1$-$C_6$ alkyl e.g. methyl, ethyl, n-propyl, isopropyl, n-butyl, iso-, sec- or t-butyl etc.), aryl (e.g phenyl, benzyl, napthyl etc) or other functional groups, preferably with at least one heteroatom and preferably having no more than 10 atoms in total, more preferably no more than 6.

Particularly preferred somatostatin analogues are constrained peptides of 6 to 10 α-amino acids, of which particular examples include octreotide, lanreotide (of sequence $NH_2$-(D)Naph-Cys-Tyr-(D)Trp-Lys-Val-Cys-Thr-$CONH_2$ (SEQ ID NO: 3) and its cyclic derivative of sequence $NH_2$-(D)Naph-Cys-Tyr-(D)Phe-Lys-Val-Cys-Thr-$CONH_2$ (SEQ ID NO: 4) both having a Cys-Cys intramolecular disulphide crosslink), SOM 230 (see structure below) and vapreotide. Most preferred is octreotide.

Structure of SOM230

(SEQ ID NO: 5)

The somatostatin analogue will generally be formulated as 0.1 to 10% by weight of the total formulation. Typical values will be 1 to 9%, preferably 2 to 9% and more preferably 2.5 to 8%. A somatostatin analogue content of around 6% is most preferable.

Doses of the somatostatin analogue suitable for inclusion in the formulation, and thus the volume of formulation used will depend upon the release rate (as controlled, for example by the solvent type and amount use) and release duration, as well as the desired therapeutic level, the activity and the rate of clearance of the particular active chosen. Typically an amount of 1 to 500 mg per dose would be suitable for providing a therapeutic level for between 7 and 90 days. This will preferably be 5 to 300 mg. For octreotide, the level will typically be around 10 to 180 mg (e.g. for a 30 to 90 day duration). Preferably, the amount of octreotide will be around 0.2 to 3 mg per day between injections. Thus a depot administered every 30 days would have 6 to 90 mg or a 90 day depot have 18 to 270 mg of octreotide.

One of the surprising advantages of the specific peptide salts indicated herein is that they allow for an extremely gradual release of active agent and thus a depot composition containing a large amount of active for release over a long period. Release durations of, for example, up to 180 days are thus within the reach of the compositions of the invention and, doses of up to 1 g of active agent may be necessary for such long-acting depots.

For ease of reference, terms such as "peptide", "somatostatin analogue", "octreotide" and other peptides are used and referred to herein. In the present invention, this reference is to the halide (e.g. chloride or bromide or mixture thereof) salt where context allows rather than to the free peptide, or is to the peptide cation, where one or more anionic counter-ions is indicated.

The pre-formulations of the present invention are formulated to be administered parenterally. This administration will generally not be an intra-vascular method but will preferably be subcutaneous intracavitary or intramuscular. Typically the administration will be by injection, which term is used herein to indicate any method in which the formulation is passed through the skin, such as by needle, catheter or needle-less injector.

Preferred parenteral administration will depend upon the particular slow-release formulation used in the invention. For the preferred lipid depot systems, for example, it is preferable to administer the preformulation by i.m or s.c. injection, most preferably by deep s.c. injection. This has the advantage of being less deep and less painful to the subject than the (deep) i.m. injection used for administration of polymer-type octreotide depots and is technically most suitable in the present case as it combines ease of injection with low risk of skin side effects. Evidently, for polymer-type depot compositions, i.m. injection is preferred.

The pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives.

In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the preformulations of the present invention are of low viscosity. As a result, these preformulations must not be in any bulk liquid crystalline phase since all liquid crystalline phases have a viscosity significantly higher than could be administered by syringe or spray dispenser. The preformulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "non-swollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse and/or degrade, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion) and take in aqueous fluid from the bodily environment (e.g. the in vivo environment) such that at least a part of the formulation generates a non-lamellar, particularly liquid crystalline phase structure. In most cases these non-lamellar structures are highly viscous and are not easily dissolved or dispersed into the in vivo environment. The result is a monolithic "depot" generate in vivo with only a limited area of exposure to body fluids. Furthermore, because the non-lamellar structure has large polar, apolar and boundary regions, it is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

The depot systems formed by the formulations of the present invention are highly effective in protecting the active agent from degradation and thus allow an extended release period. Comparative tests have been carried out between the known PLGA slow-release product and formulations of the present invention containing GDO, soy PC, ethanol and octreotide. These indicate that formulations of the present invention give lesser degradation under simulated in vivo conditions than known compositions of octreotide with PLGA microspheres. The formulations of the invention thus may provide in vivo depots of somatostatin analogues which require administration only once every 20 to 90 days, preferably 30 to 60 days, more preferably 35 to 48 days. Evidently, a longer stable release period is desirable for patient comfort and compliance as well as demanding less time from health professionals.

A considerable advantage of the lipid-based depot precursors preferred in the present invention is that they are stable homogeneous phases. That is to say, they may be stored for considerable periods (preferably at least 6 months) without phase separation. As well as providing advantageous storage, this allows for the dose of somatostatin analogue to be selected by reference to the species, age, sex, weight, and/or physical condition of the individual subject, by means of injecting a selected volume. Furthermore, the present inventors have surprisingly found that the dose of active agent is proportional to the volume of composition injected, in ranges of at least 10-fold in sample volume injection (see examples and figures below). This is highly unexpected because a 10-fold increase in depot weight will not provide a corresponding increase in surface area (the area of an object increasing to the two-third power of the increase in volume) and so release would be expected to be less than 10-times enhanced. Even in situations where dosing is not directly proportional to injection volume, however, the homogeneous nature of the depot precursors allow for partial administration of a pre-measured dose and this administration may be made by reference to a dosing table, chart, software calculation etc. which may take into account any or all relevant subject variables.

In the lipid-depot embodiment, the present invention thus provides for methods comprising the selection of a dosing amount specific to an individual, particularly by subject weight. The means for this dose selection being by administration volume.

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water. In fact, pre-formulations of the invention have shown considerably less of an initial "burst" than previously known polymer-base depot compositions which tend to have an initial "wash off" of surface-bound active agent. This is illustrated in the Examples below and Figures attached hereto. In one embodiment, the invention thus provides injectible preformulations and resulting depot compositions wherein the highest plasma concentration of active after administration is no more than 10 times the average concentration between 24 hours and 5 days of administration. This ratio is preferably no more than 8 times and most preferably no more than 5 times the average concentration.

The compositions of the invention (especially those using the preferred lipid depot systems) also allow for the generation of depot compositions with very little "lag" effect after administration. In a further embodiment, the invention thus provides injectible preformulations and resulting depot compositions wherein the plasma concentration of active at 7 days after a single administration is no lower than the plasma concentration of active at 21 days after administration. Similarly, the concentration of active should be higher at all times in the first 21 days than the concentration at any time from 30 days after administration onwards. This gradually decaying release profile has not previously been demonstrated for a somatostatin analogue formulation.

The compositions of the present invention wherein the peptide active agent is in the form of a halide salt (e.g. chloride or bromide) show surprisingly advantageous release profiles in comparison with the same formulations using the more common salts such as acetate. The release rate may be up to around 4 times slower for the chloride salt than the acetate (e.g. for octreotide) and thus a depot composition may potentially be provided with up to four times the effective duration. This is obviously of considerable benefit and is highly unexpected when it is considered that only the counter-ion is changed and the actual functional peptide ion remains identical. No consideration is thought to have ever previously been given to the potential advantages of such salts in slow-release compositions.

Without being bound by theory, it is believed that the counter-ion permeability in the matrix of the slow-release composition may be responsible for this difference. This would suggest that the chloride ion, for example, permeates the depot compositions more slowly than the acetate ion.

The following features are preferred, both individually and in combination, in the various aspects of the invention:

The sustained-release delivery vehicle is a biodegradable polymer (such as polylactate, polyglycolate or PLGA) or a lipid-based slow release formulation including those described herein.

The peptide active agent is at least one somatostatin analogue salt selected from the halides of those indicated herein, preferably of octreotide, lanreotide, SOM230, or vapreotide;

Component a comprises, consists essentially of or preferably consists of GDO;

Component b comprises, consists essentially of or preferably consists of soy PC;

Component c comprises, consists essentially of or preferably consists of a 1, 2, 3 or 4 carbon alcohol, preferably isopropanol or more preferably ethanol;

The preformulation has a low viscosity as indicated herein.

The preformulation forms a liquid crystalline phase as indicated herein upon in vivo administration.

The preformulation generates a depot following in vivo administration, which depot releases at least one somatostatin analogue at a therapeutic level over a period of at least 30 days, preferably at least 40 days, more preferably at least 60 days.

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 19 gauge, preferably smaller than 19 gauge, more preferably 23 gauge;

The method comprises a single administration every 20 to 180 days, preferably 30 to 60 days, more preferably 35 to 48 days.

In combination with the features and preferred features indicated herein, the use(s) of the preformulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 19 gauge, preferably smaller than 19 gauge, more preferably 23 gauge or smaller;

The use comprises the manufacture of a medicament for administration once every 20 to 180 days, preferably 30 to 60 days, more preferably 35 to 48 days.

In combination with the features and preferred features indicated herein, the pre filled devices of the invention may have one or more of the following preferred features independently or in combination:

They contain a preferred formulation as indicated herein;

They comprise a needle smaller than 19 gauge, preferably no larger than 23 gauge;

They contain a single dose of 1 to 1000 mg of somatostatin analogue salt, preferably 5 to 300 mg;

They contain octreotide chloride, at around 10 to 180 mg;

They contain octreotide chloride at around 0.2 to 3 mg per day between scheduled administrations;

They contain a total volume for administration of no more than 5 ml, preferably no more than 3 ml more preferably no more than 2 ml.

In combination with the features and preferred features indicated herein, the kits of the invention may have one or more of the following preferred features independently or in combination:

They contain a preferred formulation as indicated herein;

They contain a prefilled device as indicated herein;

They contain a needle no larger than 19 gauge, preferably no larger than 23 gauge;

They contain a single dose of 1 to 1000 mg of somatostatin analogue salt, preferably 5 to 300 mg;

They contain octreotide chloride, at around 10 to 180 mg;

They contain octreotide chloride at around 0.2 to 3 mg per day between scheduled administrations;

They contain a total volume for administration of no more than 5 ml, preferably no more than 3 ml more preferably no more than 2 ml.

They contain instructions for administration by a route and/or at a frequency as indicated herein;

They contain instructions for administration for use in a method of treatment as described herein.

The invention will now be further illustrated by reference to the following non-limiting Examples and the attached Figures, in which.

EXAMPLES

Example 1

Availability of Various Liquid Crystalline Phases in the Depot by Choice of Composition Injectable formulations containing different proportions of phosphatidyl choline ("PC"—Epikuron 200) and glycerol dioleate (GDO) and with EtOH as solvent were prepared to illustrate that various liquid crystalline phases can be accessed after equilibrating the depot precursor formulation with excess water.

Appropriate amounts of PC and EtOH were weighed in glass vials and the mixture was placed on a shaker until the PC completely dissolved to form a clear liquid solution. GDO was then added to form an injectible homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in H$_2$O |
|---|---|---|---|---|
| A | 22.5 | 67.5 | 10.0 | L$_2$ |
| B | 28.8 | 61.2 | 10.0 | I$_2$ |
| C | 45.0 | 45.0 | 10.0 | H$_{II}$ |
| D | 63.0 | 27.0 | 10.0 | H$_{II}$/L$_\alpha$ |

L$_2$ = reversed micellar phase
I$_2$ = reversed cubic liquid crystalline phase
H$_{II}$ = reversed hexagonal liquid crystalline phase
L$_\alpha$ = lamellar phase Example 2

Viscosity in PC/GDO (5:5) or PC/GDO (4:6) on Addition of Solvent (EtOH, PG and NMP)

A mixture of PC/GDO/EtOH with approximately 25% EtOH was manufactured according to the method in Example 1. All, or nearly all, of the EtOH was removed from the mixture with a rotary evaporator (vacuum, 40° C. for 1 h followed by 50° C. for 2 h) and the resulting mixture was weighed in a glass vial after which 1, 3, 5, 10 or 20% of a solvent (EtOH, propylene glycol (PG) or n-methylpyrrolidone (NMP)) was added. The samples were allowed to equilibrate several days before the viscosity was measured with a CarriMed CSL 100 rheometer equipped with automatic gap setting.

This example clearly illustrates the need for solvent with certain depot precursors in order to obtain an injectable formulation (see FIG. 1). The viscosity of solvent-free PC/GDO mixtures increases with increasing ratio of PC. Systems with low PC/GDO ratio (more GDO) are injectable with a lower concentration of solvent.

Example 3: Preparation of Depot Composition Containing the Peptide Octreotide

Octreotide acetate (24 mg or 60 mg) was dissolved in 0.1 g EtOH. 0.36 g PC and 0.54 g GDO were subsequently dissolved in this solution and a depot formulation precursor was obtained. Injecting the formulation precursor into excess aqueous phase (syringe 23G; 0.6 mm×30 mm) resulted in a monolithic liquid crystalline phase (I$_2$ structure). I.e. octreotide (2.4% or 6.0%) did not change monolith formation and phase behaviour after exposure to an aqueous environment.

The octreotide depot precursor formulations in this Example were tested for stability against crystallization during storage. Each formulation was stable at 4-8° C. for at least two weeks.

Example 4: Preparation of Octreotide Chloride Salt

Octreotide chloride (OCT(Cl)) was prepared from Octreotide acetate (OCT(Ac)) by running an aqueous solution of OCT(Ac) through an ion-exchange column, pre-packed with the anion-exchange resin Dowex 1×2 (Fluka) and pre-equilibrated with water for injection (WFI). The adequate fractions of OCT(Cl) in WFI were identified by measuring the conductivity of the collected fractions. These fractions were pooled and the sample was lyophilized by freeze-drying overnight giving the OCT(Cl) as a white powder.

Example 5: Octreotide Acetate and Octreotide Chloride Compositions

Liquid crystalline formulations of OCT(Ac) and OCT(Cl) were prepared in the following way: Soy phosphatidylcholine (SPC—Lipoid S100 from Lipoid, Germany), glycerol dioleate (GDO—from Danisco, Denmark), ethanol (EtOH 99.5%) and OCT(Ac) (PolyPeptide Labs, CA, USA) or OCT(Cl) (as prepared in Example 4) were mixed in excess EtOH until a homogenous liquid mixture was obtained. The EtOH content was thereafter adjusted to 5 wt % by rotary evaporation of the excess solvent. The sample compositions are given in the Table below:

| Formulation compositions in wt %. | | | | | |
|---|---|---|---|---|---|
| Formulation# | OCT(Ac) | OCT(Cl) | SPC | GDO | EtOH |
| 186 | 3 | — | 46 | 46 | 5 |
| 183 | — | 3 | 46 | 46 | 5 |

The in vitro release was determined by first placing a sample of the respective formulation (0.1-0.4 g) in a well of a 96-deep-well plate. After allowing the liquid octreotide formulation to settle in the bottom of the well for a few minutes, phosphate buffered saline (PBS) was added in different amounts (0.2-1 mL) to achieve the required conditions with respect to the formulation-to-aqueous medium weight ratio (from formulation in excess to PBS in excess). The 96-well plate was thereafter put on a shaking table held at 37° C. and with low rotating speed (150 rpm). After 24 hours, PBS samples from the respective wells were withdrawn and the octreotide content (in terms of octreotide base=OCT(O)) in the aqueous release medium was analyzed by HPLC. At least two replicates (wells) for each formulation-to-PBS ratio and for each formulation were analyzed.

Figure 2:
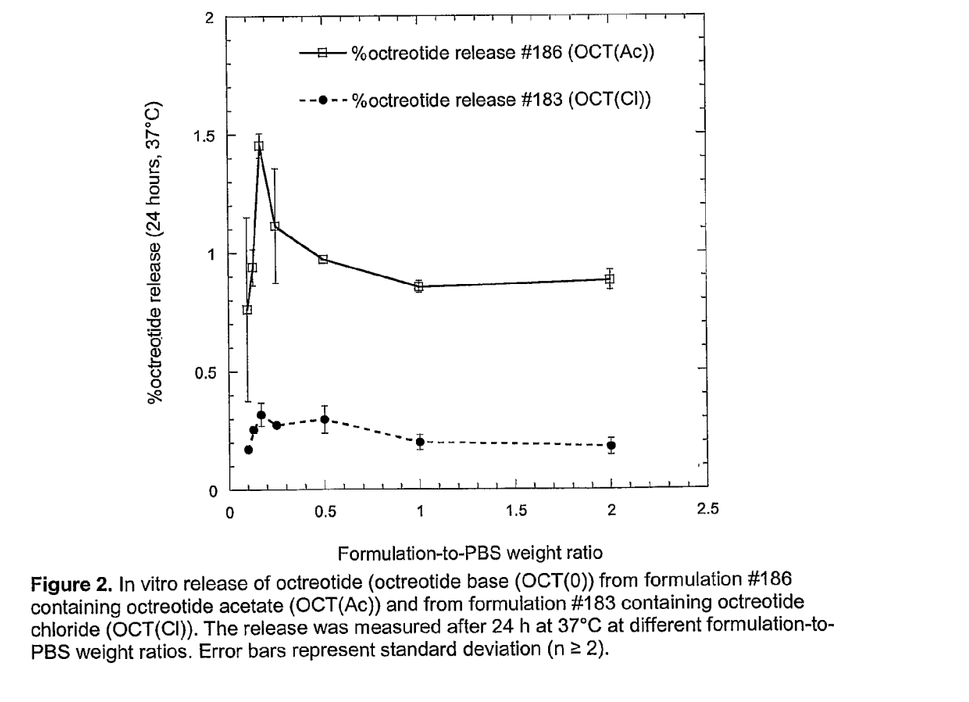
FIG. 2 shows in vitro release of octreotide (octreotide base (OCT(O)) from a formulation containing octreotide acetate (OCT(Ac)) and from a formulation containing octreotide chloride (OCT(Cl)).

The results are shown in FIG. 2 as % octreotide (octreotide base=OCT(O)) released from the respective formulation as a function of formulation-to-PBS weight ratio. It is clear from FIG. 2 that under all the investigated conditions in terms of formulation-to-PBS weight ratios, the release of octreotide from the formulation containing OCT(Ac) is markedly higher than for the corresponding OCT(Cl) formulations. This fact is highly surprising considering that only the peptide counter-ion (acetate versus chloride) differs between the formulations. The effects observed are essentially independent of the PBS to formulation ratio and are of particular interest for a long-acting release depot product of octreotide (e.g. 1 month or longer duration) where a slow release of the peptide active agent is a pre-requisite.

Example 6: Stability of Octreotide in LC Depot Formulation—Comparison Between Octreotide Acetate (OCT(Ac)) and Octreotide Chloride (OCT(Cl))

Experimental Details

LC formulations of OCT(Ac) and OCT(Cl) were prepared as described above in Example 5. (OCT(Cl) was prepared from OCT(Ac) by ion-exchange column chromatography—see Example 4). The compositions of the formulations are given in the Table below. The formulations were stored in glass vials with Teflon®-coated rubber stoppers in a climate chamber (Termak) at 40° C./75% relative humidity. The octreotide content (expressed as % of nominal content), ID and related substances were determined by HPLC with UV detection at 215 nm.

Nominal formulation compositions in wt %.

| Formulation# | OCT(Ac) [OCT(0)] | OCT(Cl) [OCT(0)] | SPC | GDO | EtOH |
|---|---|---|---|---|---|
| 174 | 4.8 [4.1] | | 45.0 | 45.0 | 5.1 |
| 192 | | 5.5 [4.9] | 44.7 | 44.7 | 5.1 |

Results

Figure 3:
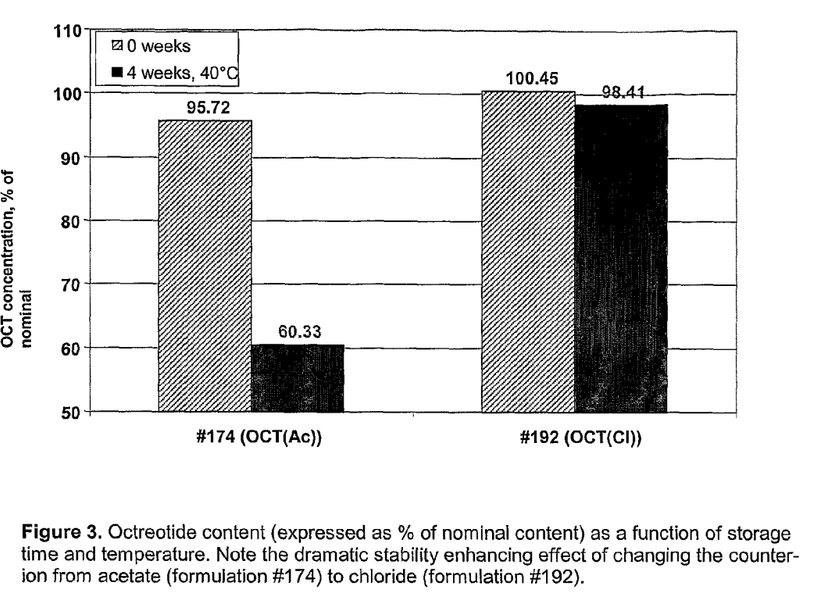
FIG. 3. shows the octreotide content (expressed as % of nominal content) as a function of storage time and condition for acetate and chloride formulations.
Figure 4:
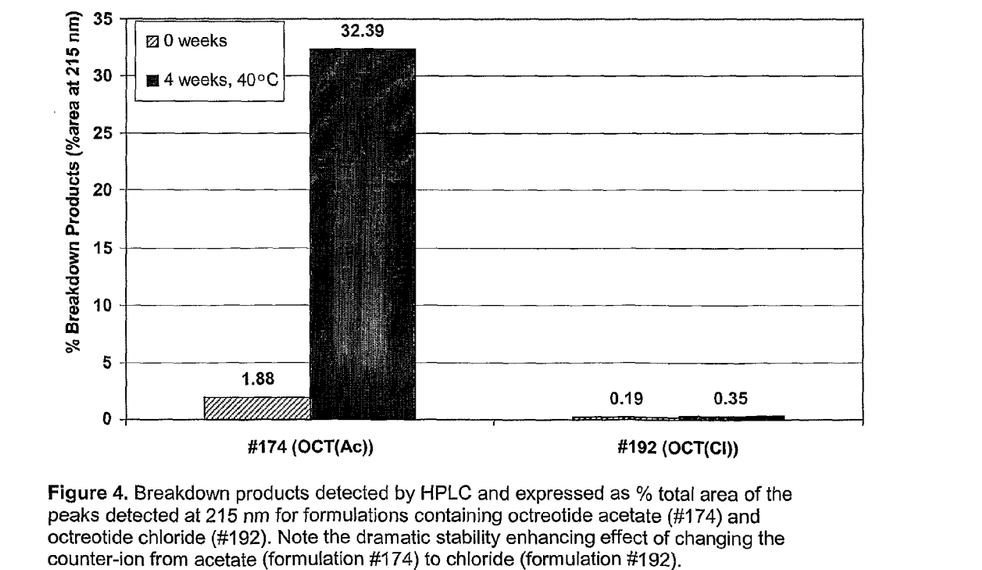
FIG. 4. shows the breakdown products detected by HPLC and expressed as % area at 215 nm for formulations containing octreotide acetate and octreotide chloride.

The octreotide content, expressed as % of nominal concentration (see Table 2), as a function of storage time and condition is shown in FIG. 3. The effect of changing the counter-ion from acetate to chloride is unexpectedly high. Whereas little change occurs for the OCT(Cl) formulation (#192) after 4 weeks at 40° C., a marked degradation of octreotide in the OCT(Ac) formulation (#174) takes place. This is even more clearly seen in FIG. 4 where the amount of breakdown products (expressed as % of the total Peak Area at 215 nm UV detection) is displayed as a function of storage time and condition. In conclusion, the stability enhancing effect of the chloride counter-ion is surprisingly high which is extremely beneficial from a storage stability perspective of a depot formulation product of octreotide.

Example 7: Further Examples of Viscosity in PC/GDO Mixtures on Addition of Co-Solvent Mixtures of PC/GDO and co-solvent were prepared according to the methods of Example 1 and Example 2 in the proportions indicated in the table below.

The samples were allowed to equilibrate for several days before viscosity measurements were performed using a Physica UDS 200 rheometer at 25° C.

| Sample | PC/GDO (wt/wt) | EtOH/ wt % | Glycerol/ wt % | $H_2O$/ wt % | Viscosity/ mPas |
|---|---|---|---|---|---|
| 1 | 50/50 | 3 | — | — | 1900 |
| 2 | 50/50 | 5 | — | — | 780 |
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8*10^6$ |
| 20 | 40/60 | — | — | 3 | $2.5*10^8$ |
| 21 | 40/60 | — | — | 5 | $4*10^7$ |

This example further illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

The invention claimed is:

1. A ready-to-use pre-formulation comprising a low viscosity mixture of:
   a) 40 to 60 wt % of glycerol dioleate (GDO);
   b) 40 to 60 wt % of at least one phosphatidyl choline;
   c) 3 to 10 wt % ethanol; and
   d) 1 to 8 wt % octreotide chloride;
   wherein the ratio of a:b (w/w) is 48:52 to 55:45;
   wherein the pre-formulation is stable to storage at room temperature for at least 6 months without loss of more than 10% of the activity of octreotide chloride before storage; and
   wherein the pre-formulation forms, or is capable of forming, at least one liquid crystalline phase structure upon contact with an aqueous fluid.

2. The pre-formulation according to claim 1, wherein component b) comprises soy phosphatidyl choline (soy PC).

3. A disposable administration device pre-loaded with a measured dose of the pre-formulation comprising a low viscosity mixture of claim 1.

4. The device according to claim 3, wherein said device is a syringe or syringe barrel.

5. The device according to claim 3, wherein said device contains a single dose of 1 to 1000 mg of octreotide chloride.

6. The device according to claim 5, wherein said device contains octreotide chloride, in an amount ranging from about 10 to 360 mg.

7. The device according to claim 3, wherein said device contains octreotide chloride in an amount ranging from about 0.2 to 3 mg per day between scheduled administrations.

8. The device according to claim 3, wherein said device contains a total volume for administration of no more than 5 ml.

9. A kit for the administration of octreotide chloride, said kit containing a measured dose of the pre-formulation of claim 1.

10. The kit according to claim 9, further comprising an administration device.

11. The kit according to claim 10, wherein the administration device is a disposable administration device pre-loaded with a measured dose of the pre-formulation.

12. The kit according to claim 9, wherein said kit contains instructions for administration by intramuscular (i.m.), subcutaneous (s.c.) or deep s.c. injection.

13. The kit according to claim 9, wherein said kit contains instructions for administration for use in a method of treatment of a human or non-human mammalian subject in need thereof.

14. A pre-formulation according to claim 1 wherein octreotide chloride is present in an amount of 10 to 180 mg per dose.

15. A method for the treatment of a human or non-human mammalian subject in need thereof, said method comprising administering to said subject the pre-formulation comprising a low-viscosity mixture of claim 1.

16. The method according to claim 15, wherein the method of treatment is a method for the treatment of at least one condition selected from acromegaly, cancer, elevated growth hormone, elevated insulin-like growth factor I, varicial bleeding, chemotherapy induced gastro intestinal problems, lymphorrhea, diabetic retinopathy, thyroid eye disease, obesity, and pancreatitis.

17. The method according to claim 15, comprising administration by intramuscular (i.m.), subcutaneous (s.c.) or deep s.c. injection.

18. The method according to claim 15, comprising administration by means of a pre-filled administration device.

19. The method according to claim 15, comprising a single administration every 20 to 180 days.

20. The method according to claim 16, wherein the cancer is selected from the group consisting of a carcinoma, a melanoma, a tumour expressing at least one somatostatin receptor, a prostate cancer, a gastro-entero-pancreatic neuroendocrine tumour, a carcinoid tumour, an insulinoma, a gastrinoma, a vasoactive intestinal peptide-producing tumour and a glucagonoma.

21. The method according to claim 20, wherein the cancer is a tumour expressing at least one somatostatin receptor and is selected from a somatostatin receptor-2-positive tumour, and a somatostatin receptor-5-positive tumour.

* * * * *